(12) United States Patent
Brady et al.

(10) Patent No.: US 6,752,819 B1
(45) Date of Patent: Jun. 22, 2004

(54) DELIVERY CATHETER

(75) Inventors: Eamon Brady, Elphin (IE); Paul Gilson, Moycullen (IE); David Vale, Clontarf (IE)

(73) Assignee: Salviac Limited, Dublin (IE)

( * ) Notice: Subject to any disclaimer, the term of this patent is extended or adjusted under 35 U.S.C. 154(b) by 0 days.

(21) Appl. No.: 09/676,468

(22) Filed: Oct. 2, 2000

Related U.S. Application Data (63) Continuation of application No. PCT/IE99/00021, filed on Apr. 1, 1999.

(30) Foreign Application Priority Data

Apr. 2, 1998 (IE) .................................................. 980242

(51) Int. Cl.[7] ............................................. A61M 29/00
(52) U.S. Cl. ......................... 606/200; 606/108; 604/523
(58) Field of Search ..................... 604/96.01, 104–108, 604/523; 606/200, 159, 194, 108; 600/585, 434

(56) References Cited

U.S. PATENT DOCUMENTS

| | | |
|---|---|---|
| 2,854,983 A | 10/1958 | Baskin |
| 3,334,629 A | 8/1967 | Cohn |
| 3,540,431 A | 11/1970 | Mebin-Uddin |
| 3,692,029 A | 9/1972 | Adair |
| 3,730,185 A | 5/1973 | Cook et al. |
| 3,952,747 A | 4/1976 | Kimmell, Jr. |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,445,892 A | 5/1984 | Hussein et al. |
| 4,493,711 A | 1/1985 | Chin et al. |
| 4,512,762 A | 4/1985 | Spears |
| 4,585,000 A | 4/1986 | Hershenson |
| 4,610,662 A | 9/1986 | Weikl et al. |
| 4,611,594 A | 9/1986 | Grayhack et al. |
| 4,619,246 A | 10/1986 | Molgaard-Nielsen et al. |

(List continued on next page.)

FOREIGN PATENT DOCUMENTS

| | | |
|---|---|---|
| DE | 37 06 077 | 6/1988 |
| DE | 90 10 130 | 10/1990 |

(List continued on next page.)

OTHER PUBLICATIONS

US 6,348,062, 2/2002, Hopkins et al. (withdrawn)
Specification of Application No. 10/043,173, filed Jan. 14, 2002.

(List continued on next page.)

Primary Examiner—Michael J. Hayes
Assistant Examiner—Kevin C. Sirmons
(74) Attorney, Agent, or Firm—Finnegan, Henderson, Farabow, Garrett & Dunner LLP (57) ABSTRACT

A medical catheter for the transvascular deployment of a collapsaible medial device such as a filter has a tubular body formed by an inner tubular core surrounded by an outer thin-walled tube which is fixed to the core. The outer thin-walled tube extends outwardly beyond a distal end of the core to form a fixed thin-walled medical device embracing pod. The filter is carried on a guidewire which is slidably engagable within a central lumen of the core and the filter can be collapsed against the guidewire for loading within the pod. With the filter thus loaded within the pod the distal end of the catheter can be maneuvered through a patient's vascular system to a desired deployment site where the filter is discharged from the pod allowing the filter to expand within the blood vessel for use filtering blood flowing through the blood vessel.

43 Claims, 8 Drawing Sheets

U.S. PATENT DOCUMENTS

| | | | |
|---|---|---|---|
| 4,650,466 A | | 3/1987 | Luther |
| 4,723,549 A | | 2/1988 | Wholey et al. |
| 4,790,812 A | | 12/1988 | Hawkins, Jr. et al. |
| 4,794,928 A | | 1/1989 | Kletschka |
| 4,867,156 A | * | 9/1989 | Stack et al. ............... 606/159 |
| 4,873,978 A | | 10/1989 | Ginsburg |
| 4,926,858 A | | 5/1990 | Gifford, III et al. |
| 4,927,426 A | | 5/1990 | Dretler |
| 5,011,488 A | | 4/1991 | Ginsburg |
| 5,026,377 A | | 6/1991 | Burton et al. |
| 5,053,008 A | | 10/1991 | Bajaj |
| 5,108,419 A | | 4/1992 | Reger et al. |
| 5,122,125 A | | 6/1992 | Deuss |
| 5,178,158 A | | 1/1993 | de Toledo |
| 5,324,304 A | | 6/1994 | Rasmussen |
| 5,329,942 A | | 7/1994 | Gunther et al. |
| 5,405,329 A | | 4/1995 | Durand |
| 5,593,394 A | | 1/1997 | Kanesaka et al. |
| 5,662,671 A | | 9/1997 | Barbut et al. |
| 5,669,933 A | | 9/1997 | Simon et al. |
| 5,683,451 A | * | 11/1997 | Lenker et al. ............. 623/1.11 |
| 5,695,519 A | | 12/1997 | Summers et al. |
| 5,766,203 A | | 6/1998 | Imran et al. |
| 5,769,816 A | | 6/1998 | Barbut et al. |
| 5,769,871 A | | 6/1998 | Mers Kelly et al. |
| 5,795,322 A | | 8/1998 | Boudewijn |
| 5,800,457 A | | 9/1998 | Gelbfish |
| 5,800,525 A | | 9/1998 | Bachinski et al. |
| 5,814,064 A | | 9/1998 | Daniel et al. |
| 5,823,992 A | | 10/1998 | Salmon et al. |
| 5,827,324 A | | 10/1998 | Cassell et al. |
| 5,843,167 A | * | 12/1998 | Dwyer et al. ............. 623/1.14 |
| 5,848,964 A | | 12/1998 | Samuels |
| 5,897,567 A | | 4/1999 | Ressemann et al. |
| 5,902,334 A | * | 5/1999 | Dwyer et al. ............... 606/194 |
| 5,910,154 A | | 6/1999 | Tsugita et al. |
| 5,911,734 A | | 6/1999 | Tsugita et al. |
| 5,941,869 A | | 8/1999 | Patterson et al. |
| 5,954,745 A | | 9/1999 | Gertler et al. |
| 5,976,172 A | | 11/1999 | Homsma et al. |
| 5,993,469 A | | 11/1999 | Mckenzie et al. |
| 6,001,118 A | | 12/1999 | Daniel et al. |
| 6,027,520 A | | 2/2000 | Tsugita et al. |
| 6,042,598 A | | 3/2000 | Tsugita et al. |
| 6,053,832 A | | 4/2000 | Saito |
| 6,053,932 A | | 4/2000 | Daniel et al. |
| 6,129,739 A | | 10/2000 | Khosravi |
| 6,132,458 A | | 10/2000 | Staehle et al. |
| 6,152,946 A | | 11/2000 | Broome et al. |
| 6,171,327 B1 | | 1/2001 | Daniel et al. |
| 6,179,859 B1 | | 1/2001 | Bates et al. |
| 6,179,861 B1 | | 1/2001 | Khosravi et al. |
| 6,203,561 B1 | | 3/2001 | Ramee et al. |
| 6,214,026 B1 | | 4/2001 | Lepak et al. |
| 6,245,012 B1 | | 6/2001 | Kleshinski |
| 6,245,089 B1 | | 6/2001 | Daniel et al. |
| 6,270,513 B1 | | 8/2001 | Tsugita et al. |
| 6,277,138 B1 | | 8/2001 | Levinson et al. |
| 6,277,139 B1 | | 8/2001 | Levinson et al. |
| 6,319,242 B1 | | 11/2001 | Patterson et al. |
| 6,325,815 B1 | | 12/2001 | Kusleika et al. |
| 6,336,934 B1 | | 1/2002 | Gilson et al. |
| 6,346,116 B1 | | 2/2002 | Brooks et al. |
| 6,395,017 B1 | * | 5/2002 | Dwyer et al. ............. 623/1.11 |
| 2001/0012951 A1 | | 8/2001 | Bates et al. |
| 2001/0020175 A1 | | 9/2001 | Yassour et al. |
| 2001/0041908 A1 | | 11/2001 | Levinson et al. |
| 2001/0044632 A1 | | 11/2001 | Daniel et al. |
| 2002/0004667 A1 | | 1/2002 | Adams et al. |
| 2002/0022858 A1 | | 2/2002 | Demond et al. |
| 2002/0022860 A1 | | 2/2002 | Borillo et al. |
| 2002/0026211 A1 | | 2/2002 | Khosravi et al. |

FOREIGN PATENT DOCUMENTS

| | | |
|---|---|---|
| EP | 0 256 683 | 2/1988 |
| EP | 0533511 | 3/1993 |
| EP | 0596172 | 11/1994 |
| EP | 0743046 | 11/1996 |
| EP | 0791340 | 8/1997 |
| EP | 0827756 | 3/1998 |
| EP | 1123688 | 8/2001 |
| EP | 1127556 | 8/2001 |
| EP | 1149566 | 10/2001 |
| FR | 2 580 504 | 10/1986 |
| FR | 2 616 666 | 12/1988 |
| FR | 2 768 326 | 3/1999 |
| GB | 2020557 | 11/1979 |
| GB | 2 200 848 | 8/1988 |
| WO | WO 88/09683 | 12/1988 |
| WO | WO 89/07422 | 8/1989 |
| WO | WO 94/24946 | 11/1994 |
| WO | WO 95/34254 | 12/1995 |
| WO | WO 95/34339 | 12/1995 |
| WO | WO 96/01591 | 1/1996 |
| WO | WO 96/39998 | 12/1996 |
| WO | WO 97/03810 | 2/1997 |
| WO | WO 97/17021 | 5/1997 |
| WO | WO 97/17914 | 5/1997 |
| WO | WO 97/42879 | 11/1997 |
| WO | WO 98/24377 | 6/1998 |
| WO | WO 98/30265 | 7/1998 |
| WO | WO 98/33443 | 8/1998 |
| WO | WO 98/38920 | 9/1998 |
| WO | WO 98/39053 | 9/1998 |
| WO | WO 98/46297 | 10/1998 |
| WO | WO 98/49952 | 11/1998 |
| WO | WO 98/50103 | 11/1998 |
| WO | WO 98/51237 | 11/1998 |
| WO | WO 99/16382 | 4/1999 |
| WO | WO 99/20335 | 4/1999 |
| WO | WO 99/23976 | 5/1999 |
| WO | WO 99/25252 | 5/1999 |
| WO | WO 99/44510 | 9/1999 |
| WO | WO 99/44542 | 9/1999 |
| WO | WO 99/51167 | 10/1999 |
| WO | WO 00/16705 | 2/2000 |
| WO | WO 00/16705 | 3/2000 |
| WO | WO 00/44428 | 8/2000 |
| WO | WO 00/49970 | 8/2000 |
| WO | WO 00/56390 | 9/2000 |
| WO | WO 00/67664 | 11/2000 |
| WO | WO 00/67665 | 11/2000 |
| WO | WO 00/67666 | 11/2000 |
| WO | WO 00/67667 | 11/2000 |
| WO | WO 00/67668 | 11/2000 |
| WO | WO 00/67669 | 11/2000 |
| WO | WO 00/67670 | 11/2000 |
| WO | WO 00/67671 | 11/2000 |
| WO | WO 00/67829 | 11/2000 |
| WO | WO 01/05329 | 1/2001 |
| WO | WO 01/08742 | 2/2001 |
| WO | WO 01/08743 | 2/2001 |
| WO | WO 01/12082 | 2/2001 |
| WO | WO 01/21100 | 3/2001 |
| WO | WO 01/35857 | 5/2001 |
| WO | WO 01/43662 | 6/2001 |
| WO | WO 01/45590 | 6/2001 |
| WO | WO 01/45591 | 6/2001 |
| WO | WO 01/45592 | 6/2001 |
| WO | WO 01/49208 | 7/2001 |
| WO | WO 01/49209 | 7/2001 |

| | | |
|---|---|---|
| WO | WO 01/49215 | 7/2001 |
| WO | WO 01/50982 | 7/2001 |
| WO | WO 01/52768 | 7/2001 |
| WO | WO 01/72205 | 10/2001 |
| WO | WO 01/80776 | 11/2001 |
| WO | WO 01/80777 | 11/2001 |
| WO | WO 01/97714 | 12/2001 |

OTHER PUBLICATIONS

Specification of Application No. 09/986,060, filed Nov. 7, 2001.

Specification of Application No. 09/985,820, filed Nov. 6, 2001.

Specification of Application No. 09/986,132, filed Nov. 7, 2000.

Specification of Application No. 09/938,548, filed Aug. 27, 2001 with Preliminary Amendment.

Specification of Application No. 09/921,596, filed Aug. 6, 2001 with Preliminary Amendment.

Specification of Application No. 09/838,545, filed April 20, 2001.

Specification of Application No. 09/986,064, filed Nov. 7, 2001.

Specification of Application No. 09/838,544, filed Apr. 20, 2001.

Specification of Application No. 09/887,893, filed Jun. 25, 2001.

* cited by examiner

DELIVERY CATHETER

This is a continuation of PCT Application No. PCT/IE99/00021, filed Apr. 1, 1999.

FIELD OF THE INVENTION

The present invention relates to a medical catheter and more particularly to a catheter for the transvascular deployment of expandable medical devices, such as an intravascular embolic filter device, in a collapsed condition.

BACKGROUND OF THE INVENTION

The device as described herein relates to a carotid angioplasty procedure with an intravascular filter being placed distally to capture procedural emboli being released. Other medical procedures warrant the use of distal protection systems. Angioplasty and stenting of surgically implanted Saphenous Vein grafts that have stenosed and primary treatment of Renal artery stenoses are applicable also. Indeed, the insertion of embolic protection devices to protect patients during any vascular surgery is envisioned as being applicable to this invention.

A particularly useful form of embolic protection device in the form of a filter element for placing in a desired position has been described in our co-pending patent application No. WO 99/23946 the contents of which are incorporated herein by reference. For example, this filter element is compressed into a housing or pod to advance it to the required location in a vessel. Once in situ the housing is withdrawn or the filter element is advanced. This allows the compressed filter element to expand to the required size and occlude the vessel except for the path or paths provided through the filter which thus provides a pathway for blood and has means for capturing and retaining undesired embolic material released during the surgical operation or percutaneous interventional procedure.

There are difficulties with such expandable devices, whether they be filters or other devices in that firstly they have to be correctly and efficiently compressed and retained within the pod so that when released from the pod, they will expand to assume the correct shape and will not have been distorted by the compression within the pod. The problems of distortion or incorrect expansion tend to be exacerbated if the medical device is stored for long periods within the pod prior to use. Secondly, it is important that the pod and the catheter tube itself be manipulated to the site of use without causing damage to, for example, the arteries through which it is being manipulated. Difficulties may arise if, for example, the catheter tube, or more particularly the pod as the pod effectively leads in the insertion, were to damage the artery sidewall and thus cause for example a break-away of atherosclerotic plaque from the carotid arteries.

Essentially this leads to certain requirements. The device needs to be efficiently compressed. The resulting compressed device needs to be manipulated in its pod as efficiently as possible. Further, there is a need for loading such catheters in a way that will facilitate their use on unloading.

It is known to mount implantable medical devices at a distal end of a delivery catheter for transvascular deployment. Upon reaching a desired location within a patients vasculature the catheter is withdrawn relative to the medical device thus allowing the medical device to expand or be expanded within the blood vessel. In the prior art WO98/07387 and U.S. Pat. No. 5,064,435 show stent delivery systems essentially comprising a catheter with a stent mounted in a collapsed state at a distal end of the catheter under a retractable outer sheath. An abutment within the bore of the catheter spaced proximally from the distal end of the catheter prevents retraction of the stent as the outer sheath is withdrawn over the stent. Each of these devices has at least two main components, namely an inner catheter and an outer sheath which is slidably retractable on the catheter to expose the stent for deployment.

These deployment catheters need to have lateral flexibility in order to manoeuvre through the vascalature but at the same time be sufficiently pushable so that they can be steered and manipulated through the vascalature. The mounting of a medical device within the distal end of the catheter either greatly limits the size of the medical device that can be accommodated or necessitates enlargement of the catheter which restricts access of the catheter within the vascalature of a patient.

Catheters of this type tend to be relatively long and the loading of a medical device within the distal end of the catheter prior to use can be a somewhat cumbersome operation for the surgeon. The length of the catheters makes them unwieldy and difficult to keep sterile. There is also a difficulty in ensuring air is excluded from the medical device and catheter during loading.

The present invention is directed towards overcoming these problems.

SUMMARY OF THE INVENTION

According to the invention there is provided a catheter for the transvascular deployment of a medical device, the catheter comprising an elongate tubular body having a proximal end and a distal end, a tubular housing being formed at the distal end of the body for reception of the medical device, a deployment means for engagement with the medical device, being movable through the housing to move the medical device between a stored position within the housing and an in-use position externally of the housing, characterised in that the housing comprises a tubular thin-walled medical device embracing pod fixed at the distal end of the body, the pod extending outwardly from the distal end of the body and forming an extension thereof. Conveniently, the pod and the catheter body form a single integral unit for deployment of the medical device.

Preferably the catheter body has an inner tubular core encased within a concentric thin-walled tubular outer sheath which is fixed to the core, the sheath being extended outwardly of a distal end of the core to form the pod.

The advantage of using the thin-walled tube is that the maximum volume to retain the medical device for deployment is achieved. Further the pod is relatively flexible on the catheter further facilitating its manipulation and passage through vasculature to the desired site of use.

Preferably the inner tubular core is formed from a steel spring, but may alternatively be formed from polymeric material. Any suitable material may be used as the core is now covered by the thin-walled tubular outer sheath which is effectively the important tube, being the vessel contact surface. Alternatively, a thin walled pod may be achieved by locally thinning a polymeric tube at the distal end of the tube.

Preferably the thin-walled tube is manufactured from a low friction material and ideally is manufactured from polytetrafluoroethylene (PTFE) often sold under the Registered Trade Mark TEFLON. The thin walled tube may alternatively be manufactured from any other suitable thin walled material of low friction coefficient or employing a friction reducing agent or component to minimise the friction coefficient. The advantage of this is that firstly the catheter will not damage arteries, for example the carotid, knocking off atherosclerotic plaque. Further this will allow the easy removal of the implant from the catheter.

Where the outer thin walled tube is formed of PTFE, it would typically have a thickness of less than 0.004 inches (0.1 mm). The thickness of thin walled tubes of other materials may vary somewhat depending on the characteristics of the material being used.

In another aspect the invention provides a method of loading such a catheter comprising:

inserting a loading tube into the pod at a free end of the outer thin-walled tube; and compressing the medical device and delivering the compressed medical device through the loading tube into the pod.

The problem is that if one did not insert the loading tube into the pod the thin-walled tube would collapse in compression when trying to insert the medical device. The use of the loading tube prevents such collapse.

Preferably the loading tube is a further thin-walled tube which is inserted into the pod for smooth delivery of the medical device into the pod.

Ideally the medical device is compressed by delivering the filter device through a funnel and into the loading tube which is mounted at an outlet of the funnel.

In another aspect the invention provides a delivery system for transvascular deployment of a medical device, the system comprising a catheter in combination with an associated separate loading device which is operable to collapse the medical device from an expanded in-use position to a collapsed position for reception within the pod.

Preferably the loading device comprises means for radially compressing the medical device.

In a particularly preferred embodiment the loading device comprises a funnel having an enlarged inlet end and a narrowed outlet end, the outlet end being engageable within the pod.

In another embodiment, the loading device comprises a main support having a funnel-shaped bore formed from a frustoconical filter device receiving portion terminating in a cylindrical portion formed by a thin-walled loading tube projecting from the main support. This funnel-like arrangement is a very suitable arrangement of loading a pod on the catheter with a compressible filter device.

Ideally the cone angle is between 15° and 65° and preferably may be between 35° and 45°. This allows a sufficiently gentle compression of a filter device, particularly one of a polymeric material.

In one particularly preferred embodiment of the invention, the main support is formed from the material available under the trade mark "Perspex" and the thin-walled loading tube is formed from PTFE material. The Perspex gives a smooth surface.

Preferably the loading tube is mounted on the main support on a metal spigot at an outlet end of the funnel.

In a still further aspect the invention provides a pack for an elongate intravascular catheter of the type comprising a tubular body with a proximal end and a distal end, the distal end adapted for reception of a medical device, the pack comprising a tray having means for releasably holding the distal end of the catheter relative to an associated catheter loading device in a cooperative juxtaposition on the tray, the loading device being operable to collapse the medical device from an expanded in-use position to a collapsed position for reception within the pod. This facilitate raid and correct loading of a medical device within the catheter.

Preferably the tray has a liquid retaining bath formed by recess in the tray, the bath having a depth sufficient to accommodate in a totally submerged state the distal end of the catheter and a medical device for submerged loading of the medical device into the catheter.

In another embodiment the tray has a catheter holding channel communicating with the bath, the channel defining a pathway around the tray which supports the catheter in a loading position on the tray.

Preferably the means for securing the catheter within the channel comprises a number of retainers spaced-apart along the channel, each retainer comprising two or more associated projections which project inwardly from opposite side walls of the channel adjacent a mouth of the channel, the projections being resiliently deformable for snap engagement of the catheter within the channel behind the projections.

Conveniently a ramp is provided at an end of the channel communicating with the bath to direct a distal end of the catheter towards a bottom of the bath.

In another embodiment means is provided within the bath for supporting the distal end of the catheter above the bottom of the bath. Preferably said supporting means is a step adjacent the channel.

In another embodiment means is provided within the bath for supporting a catheter loading device for engagement with the distal end of the catheter to guide a medical device into the distal end of the catheter. Preferably said means comprises a recess in a side wall of the bath for reception of a funnel with an outlet pipe of the funnel directed towards the channel for engagement within the distal end of the catheter.

Ideally, it will be appreciated that the device for loading the catheter with a compressible filter device such as described above may be used in conjunction with this pack. The advantage of this is that the filter device can be submerged in a saline bath during loading into the pod which ensures that air is excluded from the filter device when loading as it would obviously cause medical complications if air was introduced to the bloodstream during an angioplasty and stenting procedure. The tray system with the catheter distal end submerged, combined with appropriately designed catheter proximal end and standard device flushing techniques can ensure a fluid filled device is introduced to the vasculature.

BRIEF DESCRIPTION OF THE DRAWINGS

The invention will be more clearly understood from the following description of some embodiments thereof, given by way of example only, with reference to the accompanying drawings, in which.

DESCRIPTION OF THE PREFERRED EMBODIMENTS

Figure 1:
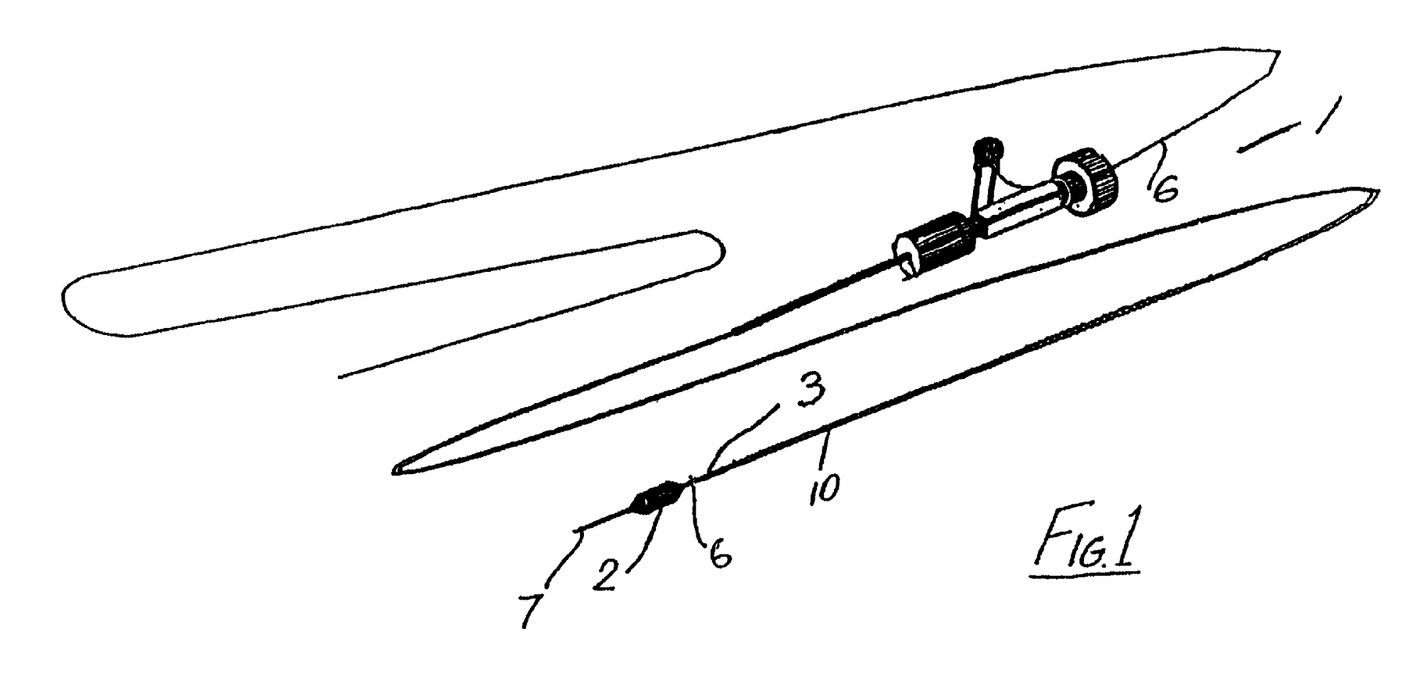
FIG. 1 is a perspective diagrammatic view of a catheter assembly according to the invention.
Figure 2:
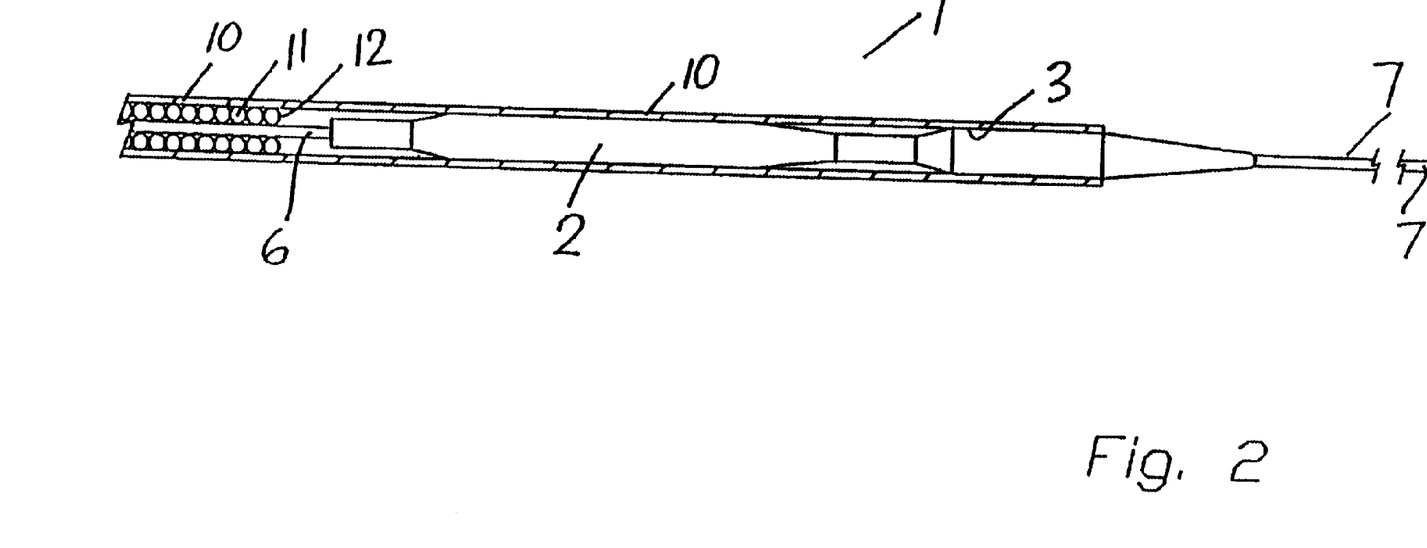
FIG. 2 is a detail partially sectioned elevational view showing an expandable filter device loaded into a distal end of the catheter.

Referring to the drawings and initially to FIGS. 1 and 2 thereof, there is illustrated a catheter, indicated generally by the reference numeral 1, for mounting a collapsible filter 2 or other collapsible medical device. The catheter has on it's free distal end a pod 3 within which the filter 2 is shown compressed in FIG. 2. A guide wire 6 on which the filter 2 is mounted is also illustrated in FIG. 2.

Figures 5, 7:
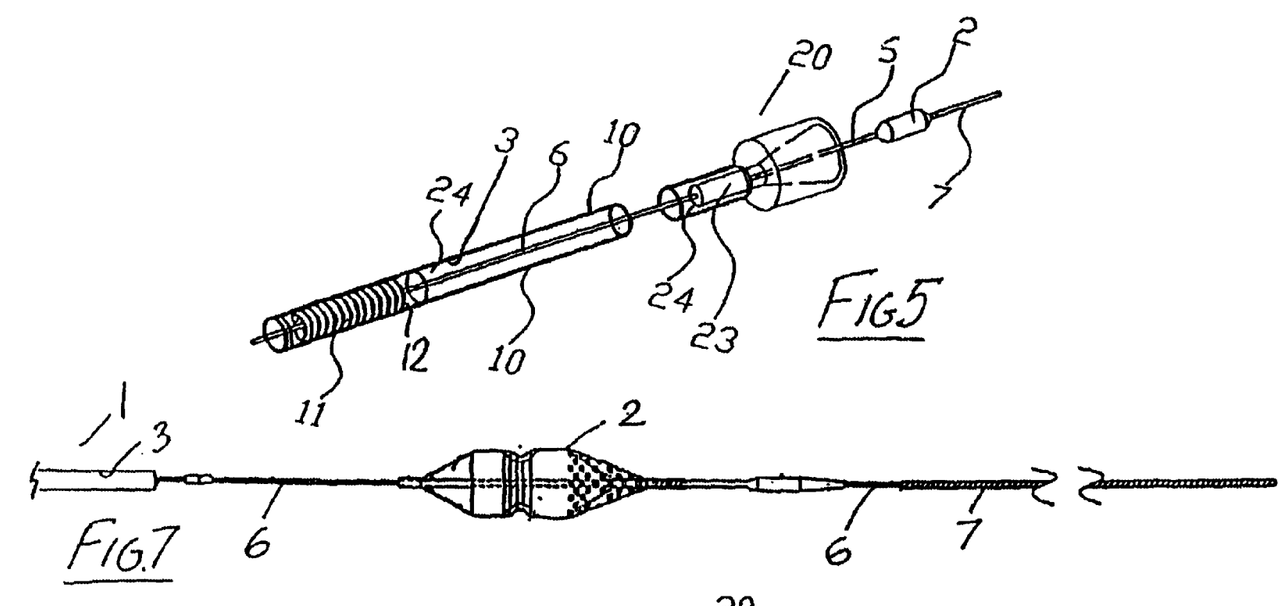
FIG. 5 is a detail diagrammatic partially sectioned perspective view showing the distal end of the catheter about to be loaded.
FIG. 7 shows the collapsible filter device 2, of the type described in our patent application No. WO 99/23976, in an expanded in-use position. The filter device 2 is mounted adjacent a distal end of the guidewire 6 which terminates at the distal end in a flexible spring tip 7.

FIG. 7 shows the collapsible filter device 2, of the type described in our patent application No. PCT/IE98/00093, in an expanded in-use position. The filter device 2 is mounted adjacent a distal end of the guidewire 6 which terminates at the distal end in a flexible spring tip 7.

The filter device can be collapsed inwardly against the guidewire 6 for reception within the pod 3 as shown in FIG. 2.

Figure 3:
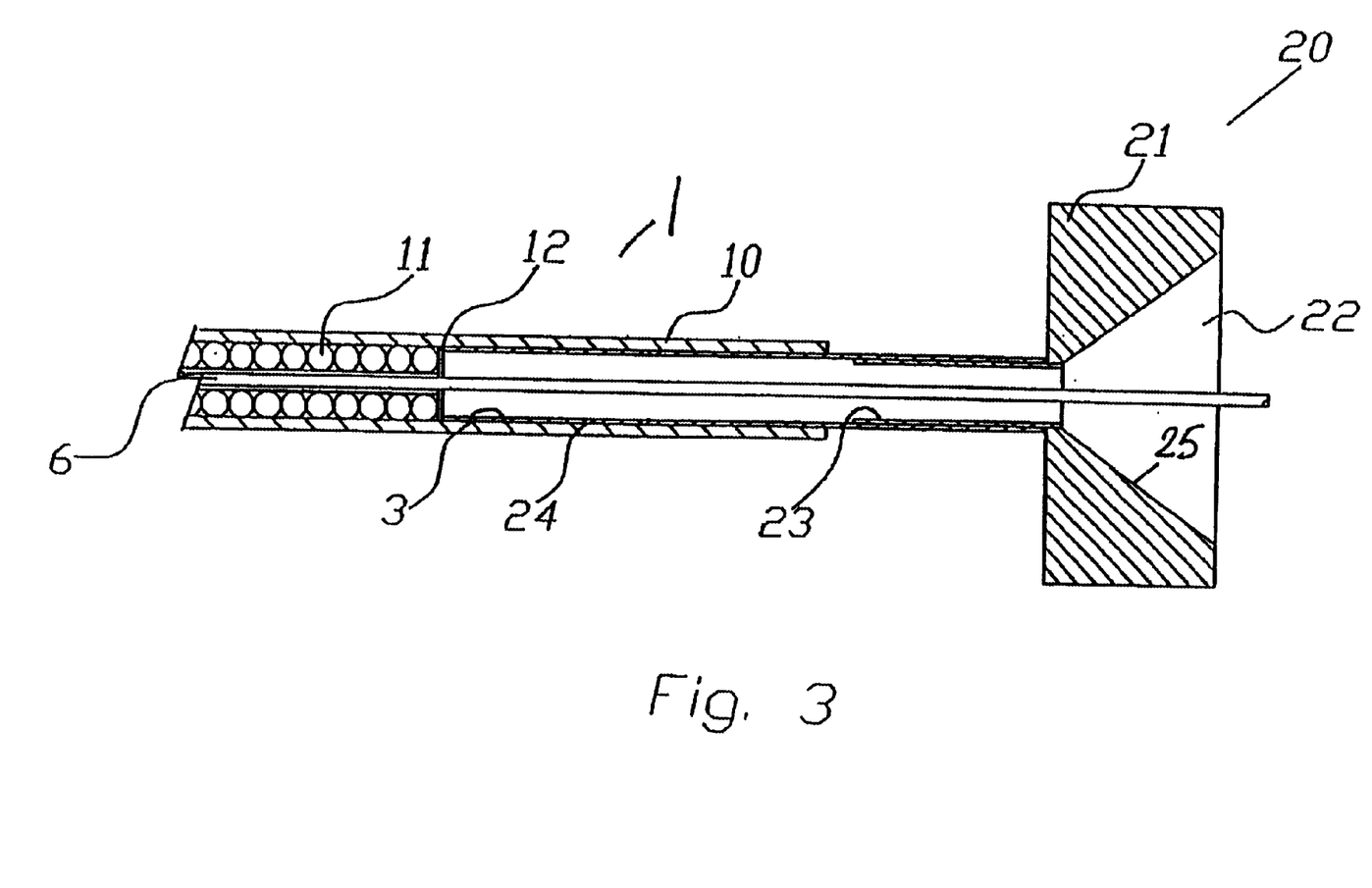
FIG. 3 is a sectional view showing a distal end portion of the catheter and a loading device for use with the catheter.
Figure 4A:
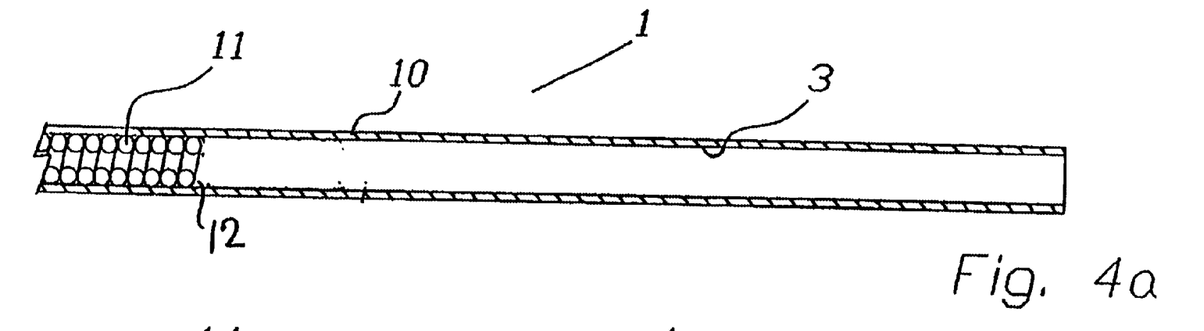
FIG. 4a is a detail sectional elevational view of the distal end portion of the catheter.

Referring particularly to FIGS. 2, 3 and 4a the catheter 1 comprises an outer thin walled tube 10 of PTFE or other thin walled polymer tube surrounding an elongate tubular body forming an inner support core which in this embodiment is formed by a spring 11. The outer thin wall tube 10 projects beyond a distal free end 12 of the spring 11 to form the pod 3.

Figure 4B:
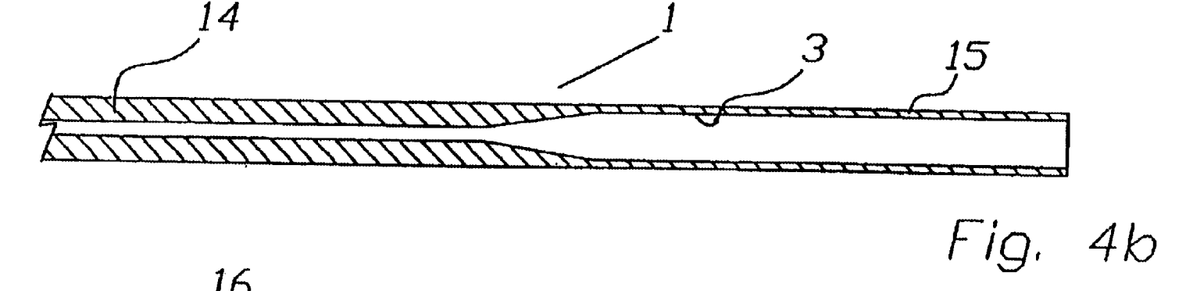
FIG. 4b is a view similar to FIG. 4a showing another catheter construction.
Figure 4C:
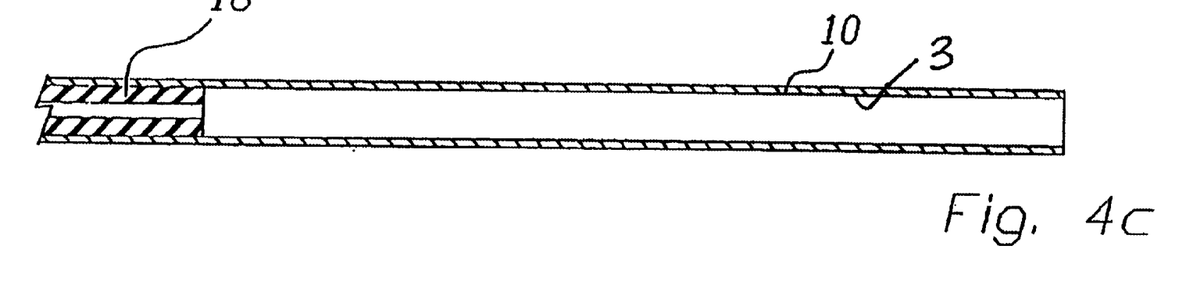
FIG. 4c is a view similar to 4a showing another catheter construction.

An alternative catheter construction is shown in FIG. 4b. In this case the catheter 1 is formed by a polymeric tube body 14 having a thin-walled distal end portion 15 which forms the pod 3. This thin-walled pod 3 is formed by locally thinning the polymeric tube body 14 at the distal end 15 of the tube body 14. A still further construction is shown in FIG. 4c in which in this case the inner support core is formed from polymeric tubing 16.

FIG. 3 also illustrates a loading device indicated generally by the reference numeral 20, which loading device comprises a support 21 having a funnel-shape bore 22 formed from a frusto-conical filter device receiving portion 25 terminating in a cylindrical portion formed by a thin wall stainless steel spigot 23 on which is mounted a loading tube 24, again of a flexible thin wall material, in this embodiment PTFE. It will be seen from FIG. 3 how the loading device 20 is inserted into the pod 3.

Figure 6:
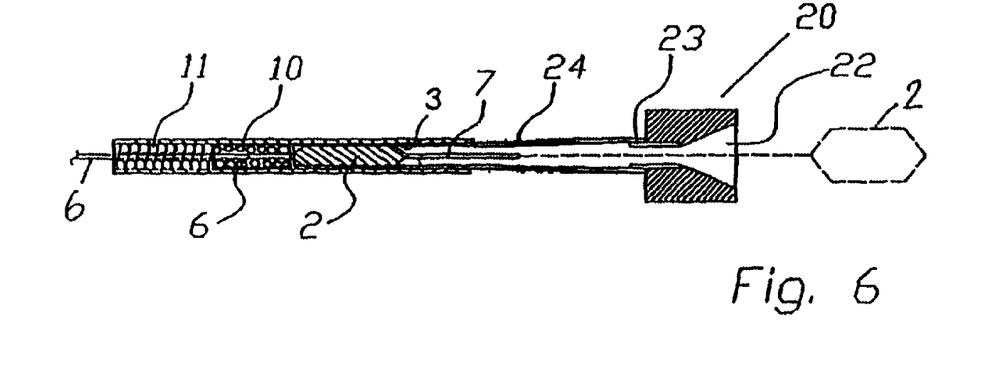
FIG. 6 is a detail sectional elevational view showing the distal end of the catheter loaded with the loading device still in position.
Figure 8:
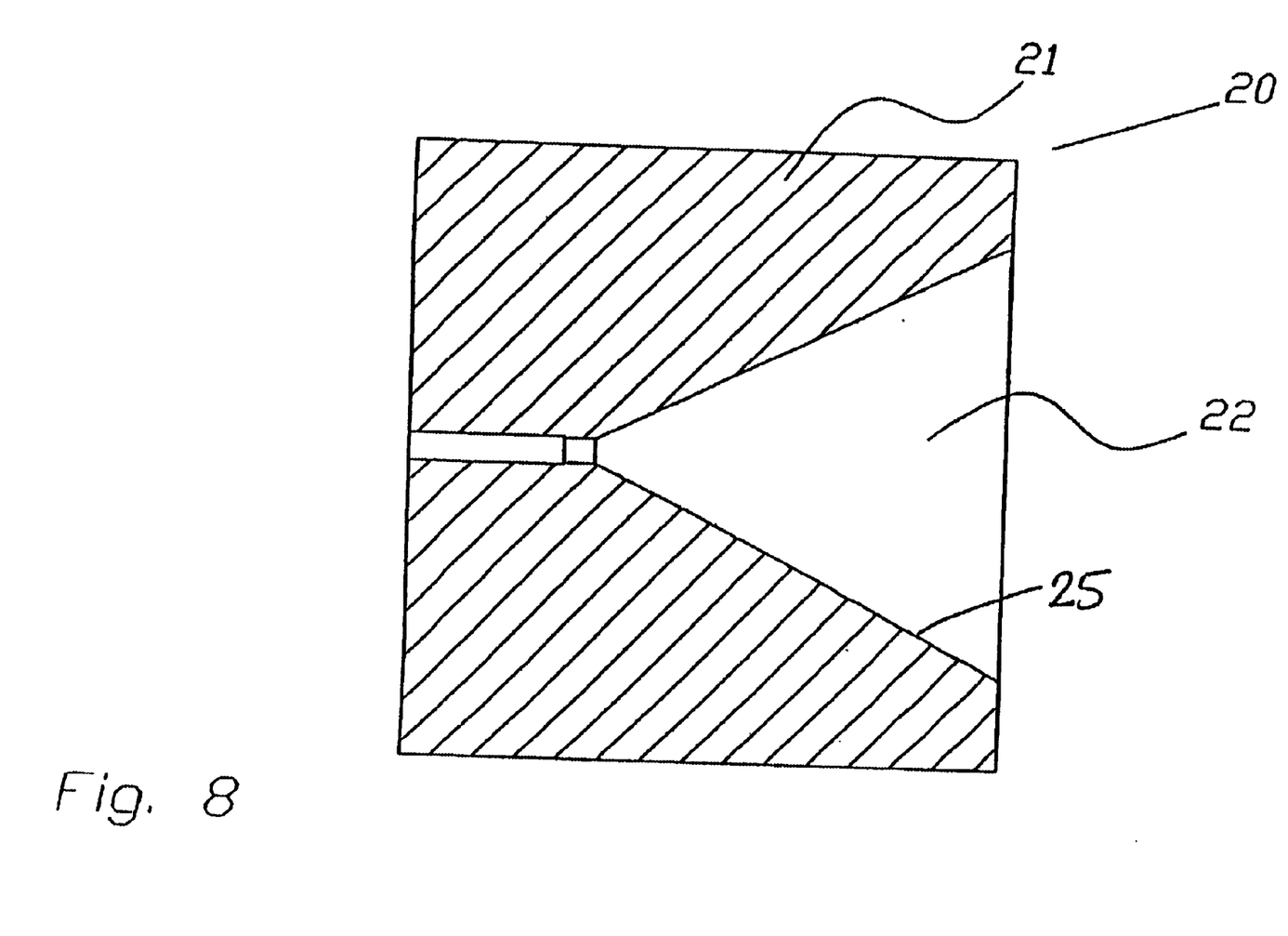
FIG. 8 is a sectional view of portion of the loading device.

To use the loading device 20, referring now specifically to FIGS. 5 and 6, the filter 2 is connected to the guidewire 6 and is drawn through the loading device 20 where it is compressed and pulled through the spigot 23 and the loading tube 24 until it rests within the pod 3 at a proximal end of the pod 3. With the guidewire 6 held fast relative to the catheter, the loading device 20 is withdrawn leaving behind the filter 2 which is now mounted within the pod 3 as shown in FIG. 2. It will be appreciated that the filter device 2 will move smoothly through the loading tube 24 as the loading tube 24 is in tension during loading.

The catheter 1 can then be delivered trans-arterially according to standard clinical practice to a deployment site. As the catheter 1 is moved through the arteries a leading end of the pod 3 which is flexible will deflect to assist in guiding the catheter 1 to the deployment site without damaging the artery wall. Once in position the filter device 2 is held stationary whilst catheter body incorporating the pod 3 is retracted. When released the filter device 2 will expand to fill the vessel.

Advantageously for use simply as a deployment catheter the thickness of the pod wall can be minimised, and consequently the crossing profile of the catheter can be minimised, as the pod does not need to be able to withstand compressive forces which would collapse the pod. When retaining the medical device and when pushing the medical device out of the pod for deployment the pod wall is in tension and so will not collapse. For loading the medical device in the pod the loading tube of the loading device projects into the pod to shield the pod from compressive forces which would collapse the pod.

It will be appreciated that instead of having the guidewire co-axially mounted within the catheter along the full length of the catheter, the guidewire may only be co-axial with an outer free end of the catheter. In this case, the guidewire is mounted alongside the catheter and enters an inlet hole adjacent the outer free end of the catheter (typically 5–20 cm from the end of the catheter) to travel coaxially within the outer free end of the catheter. This configuration is commonly referred to as a RAPID EXCHANGE system.

It will be appreciated that the catheter/pod assembly may be constructed with a single polymeric tubing that has an integral distal thin walled section describing the pod. This construction can be achieved by a localised moulding operation. Alternatively, a pod may be bonded to the. proximal tube by way of adhesive or welding.

The pod described in any of the constructions may be fabricated with enough longitudinal stiffness such that it can withstand compressive loading of a filter element into it. In this embodiment the delivery catheter may also be used as a retrieval catheter.

Referring now specifically to FIGS. 9 to 12, there is illustrated a pack for retaining a catheter assembly. Such a catheter assembly could be of conventional construction or may be as is illustrated, a catheter 1 according to the present invention.

Figure 9:
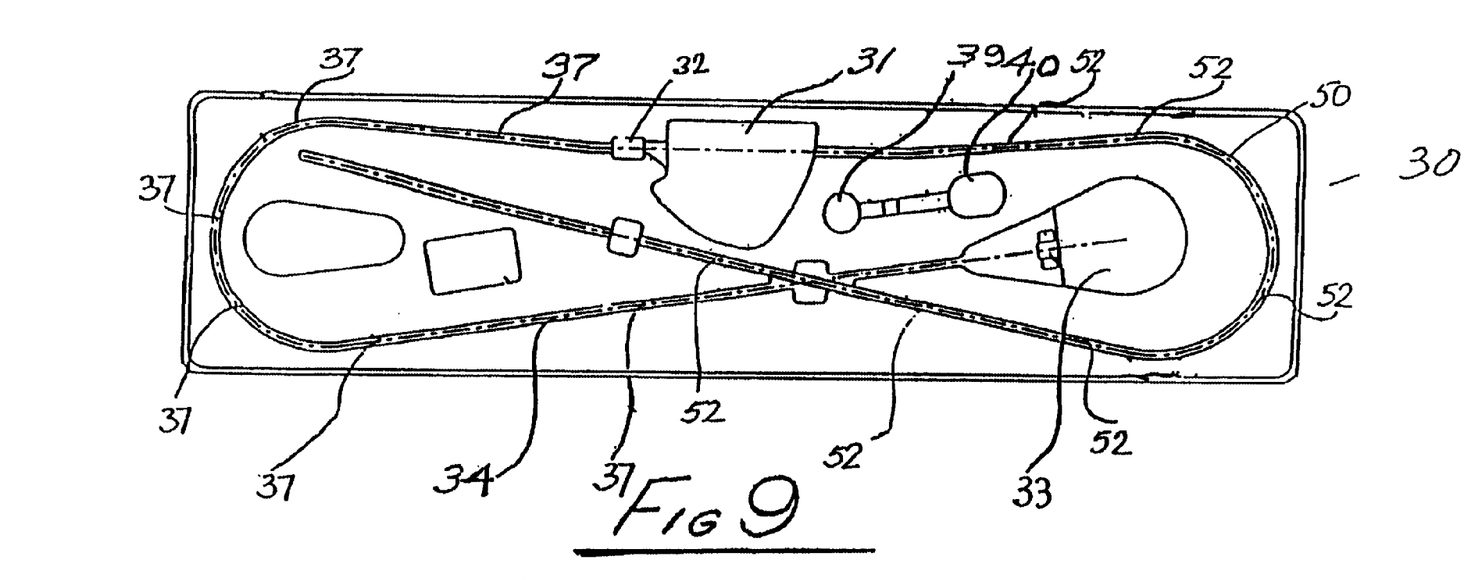
FIG. 9 is a plan view of a pack for holding the catheter assembly according to the invention, FIG. 10 are detail plan views of retaining clip portions of the pack of FIG. 9.
Figure 10:
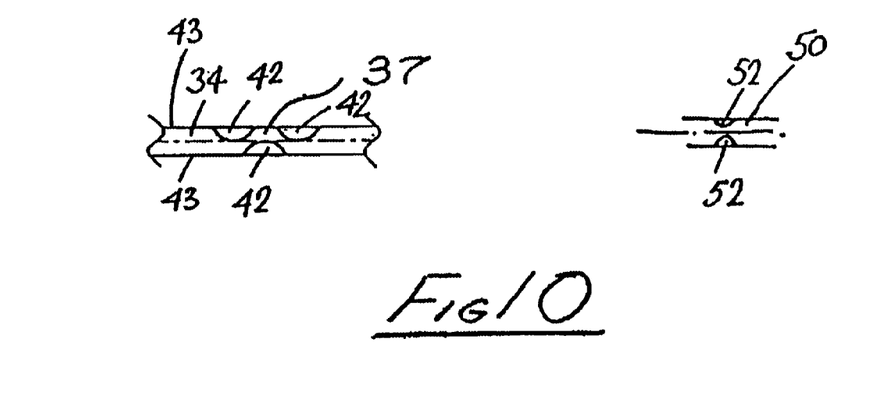

Referring to FIGS. 9 and 10 initially, the pack has a moulded plastics tray 30 which is recessed to support the parts of a catheter such as, for example, a recess 31 to retain a conventional Y-connector with an associated hub receiving slot 32 at one end for reception of a hub mounted at a proximal end of a catheter. A bath 33 is formed by another recess in the tray 30. A catheter mounting recess or channel 34 extends between the hub receiving slot 32 and the bath 33. It will be noted that the channel 34 is shaped to define a desired curve with no sharp bends and smooth transitions to facilitate loading of a catheter in situ. The channel 34 is provided with a number of spaced-apart retaining clips 37 illustrated in FIG. 10. Each retaining clip 37 comprises three associated projections 42 which project inwardly from opposite side walls 43 of the channel 34 adjacent an upwardly open mouth of the channel 34. These projections 42 and/or the side walls 43 of the channel 34 are resiliently deformable for snap engagement of a tubular catheter body within the channel 34 behind the projections 42. A downwardly sloping ramp 44 (FIG. 12) is provided at an end of the channel 34 communicating with the bath 33 to direct a distal end of a catheter 1 towards a bottom of the bath 33. Further recesses 39 and 40 respectively are provided to retain an adapter and a syringe for flushing the catheter 1 with saline solution. Obviously, it will be appreciated that many other forms of apparatus could be provided.

Figure 11:
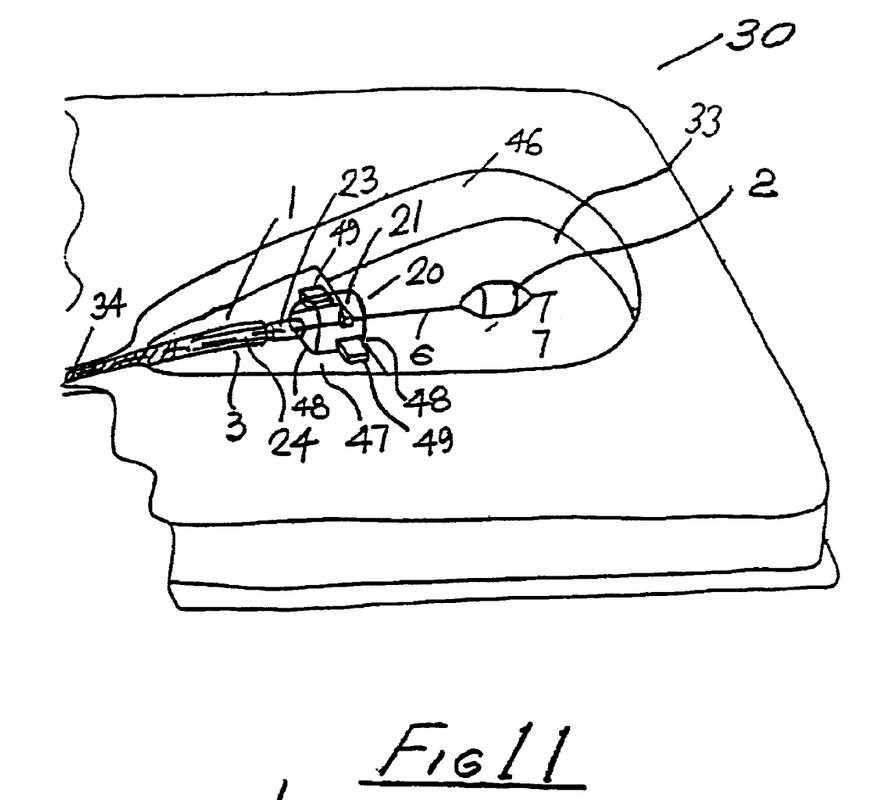
FIG. 11 is a perspective view showing a bath portion of the pack of FIG. 9.
Figure 12:
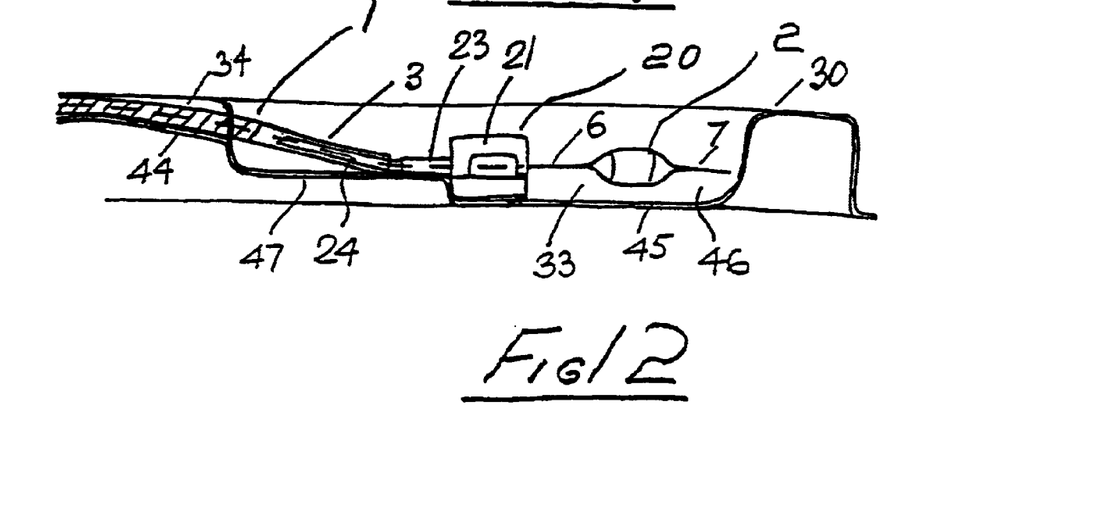
FIG. 12 is a sectional view of the bath portion of the pack illustrated in FIG. 11.

The bath 33 has a bottom 45 with an upwardly extending side wall 46. It will be noted that a step 47 is provided adjacent the channel 34 for supporting the distal end of the catheter 1 above the bottom 45 of the bath 33 to facilitate loading of the catheter 1 with a medical device 2.

A recess 48 is shaped in the step 47 for reception of the loading device 20 for the catheter 1. When the loading device 20 is mounted in the recess 48 the loading tube 24 extends into the pod 3 of the catheter 1 in a cooperating loading position. Lugs 49 at each side of the recess 48 engage and retain the support 21 in the recess 48. These lugs 49 are resiliently deformable for snap engagement of the support 21 in the recess 48 and to allow release of the support 21 from the recess 48.

A further channel 50 for a balloon tube is also provided on the tray 30 having a number of spaced-apart retaining projections 52 (FIG. 10) to retain a balloon tube in the channel 50. In use, the catheter 1 is packaged on the tray 30, being mounted within the channel 34 so it is held on the tray 30 in a position ready for loading. Saline solution is injected through the catheter 1 to exclude air from the catheter 1 and the bath 33 is filled with saline solution. The guidewire 6 having the filter 2 attached is then fed through the loading device 20 and through the catheter 1. Air is excluded from the filter 2 which is submerged in the saline bath and the filter 2 is then drawn through the loading device 20 into the pod 3 at the distal end of the catheter 1. The loading is conducted under water to prevent air entrapment in the filter device 2 whilst loading the filter device 2 in the pod 3 at the distal end of the catheter 1. It will be noted that the pod 3 at the distal end of the catheter 1 is submerged and the catheter 1 is held firmly on the tray in loading engagement with the loading device 20 while the filter 2 is being loaded into the pod 3.

The invention is not limited to the embodiments hereinbefore described which may be varied in both construction and detail within the scope of the appended claims.

What is claimed is:

1. A delivery system for transvascular deployment of a medical device comprising:
    a medical catheter assembly comprising:
        a catheter including a first portion and a second portion, the first portion including an elongate tubular body having a proximal end portion and a distal end portion, the second portion extending from the distal end portion of the first portion and forming a tubular pod capable of receiving a medical device, and
        a deployer movable through the pod and coupled to the medical device to assist in moving the medical device between a stored position within the pod and an in-use position external of the pod,
        the pod having a maximum wall thickness that is less than a minimum wall thickness of the distal end portion of the tubular body, and the pod having a greater flexibility than the distal end portion of the tubular body; and
    a separate loading device which is operable to collapse the medical device from the expanded in-use position to a collapsed position for reception within the nod, wherein the loading device comprises a funnel having an enlarged inlet end and a narrowed outlet end, the outlet end being engageable with the pod.

2. A system as claimed in claim 1 wherein the funnel comprises a main support having a funnel shaped bore and a cylindrical portion formed by a loading tube projecting from the main support.

3. A system as claimed in claim 2 in which a cone angle of the bore is between 15° and 65°.

4. A system as claimed in claim 3 in which the cone angle is between 35° and 45°.

5. A system as claimed in claim 2 in which the main support is formed from Perspex and the loading tube from polytetrafluoroethylene.

6. A system as claimed in claim 2 in which the loading tube is mounted on a spigot at the outlet end of the funnel.

7. A medical catheter pack for a delivery system for transvascular deployment of a medical device comprising:
    a delivery system for transvascular deployment of a medical device comprising:
        a medical catheter assembly comprising:
            a catheter including a first portion and a second portion, the first portion including an elongate tubular body having a proximal end portion and a distal end portion, the second portion extending from the distal end portion of the first portion and forming a tubular pod capable of receiving a medical device, and
            a deployer movable through the pod and coupled to the medical device to assist in moving the medical device between a stored position within the pod and an in-use position external of the pod,
            the pod having a maximum wall thickness that is less than a minimum wall thickness of the distal end portion of the tubular body, and the pod having a greater flexibility than the distal end portion of the tubular body; and
        a separate loading device which is operable to collapse the medical device from the expanded in-use position to a collapsed position for reception within the pod,
    the pack comprising the delivery system and a tray configured to releasably hold the pod of the catheter and the loading device in a cooperative juxtaposition on the tray, wherein the tray has a liquid retaining bath formed by a recess in the tray, the bath having a depth sufficient to accommodate, in a totally submerged state, the pod of the catheter and the medical device for submerged loading of the medical device into the pod.

8. A pack as claimed in claim 7 wherein the tray has a catheter holding channel communicating with the bath, the channel defining a pathway around the tray which supports the catheter on the tray.

9. A pack as claimed in claim 8 wherein the catheter is held within the channel by a number of retainers spaced-apart along the channel, each retainer comprising two or more associated projections which project inwardly from opposite side walls of the channel adjacent a mouth of the channel, the projections being resiliently deformable for snap engagement of the catheter within the channel behind the projections.

10. A pack as claimed in claim 8 wherein a ramp is provided at an end of the channel communicating with the bath to direct a distal end of the catheter towards a bottom of the bath.

11. A pack as claimed in claim 10 including a step adjacent the channel configured to support the pod above the bottom of the bath.

12. A pack as claimed in claim 7 wherein means is provided within the bath for supporting the distal end of the catheter above the bottom of the bath.

13. A pack as claimed in claim 7 wherein a recess provided within the bath supports the loading device for engagement with the pod to guide the medical device into the pod.

14. A pack as claimed in claim 13 wherein said recess is located in a side wall of the bath for reception of a funnel with an outlet pipe of the funnel directed towards the channel for engagement with the pod of the catheter.

15. A medical catheter assembly for the transvascular deployment of a medical device, the assembly comprising:
a catheter including a first portion and a second portion, the first portion including an elongate tubular body having a proximal end portion, a distal end portion, and a helically wound spring forming an inner tubular core encased within a concentric tubular outer sheath which is fixed to the core, and
the second portion formed by a portion of the sheath extending from the distal end portion of the first portion and forming a tubular pod capable of receiving a medical device; and
a deployer movable through the pod and coupled to the medical device to assist in moving the medical device between a stored position within the pod and an in-use position external of the pod,
the pod having a maximum wall thickness that is less than a minimum wall thickness of the distal end portion of the tubular body, and the pod having a greater flexibility than the distal end portion of the tubular body.

16. A catheter assembly as claimed in claim 15 wherein the pod is integrally formed with the tubular body.

17. A catheter assembly as claimed in claim 15 wherein the pod has sufficient axial rigidity to allow retraction of the medical device directly into the pod.

18. A catheter assembly as claimed in claim 15 wherein the wall thickness of the pod is less than or equal to 0.004 inches (0.1 mm).

19. A catheter assembly as claimed in claim 15 in which the tubular outer sheath is manufactured from a relatively low friction material.

20. A catheter assembly as claimed in claim 15 wherein the tubular outer sheath incorporates a friction reducing agent.

21. A catheter assembly as claimed in claim 15 wherein the tubular outer sheath has a composite friction reducing structure.

22. A delivery system for transvascular deployment of a medical device, the system comprising a catheter assembly as claimed in claim 15 in combination with a separate loading device which is operable to collapse the medical device from the expanded in-use position to a collapsed position for reception within the pod.

23. A system as claimed in claim 22 wherein the loading device comprises means for radially compressing the medical device.

24. A medical catheter pack for a delivery system of the type claimed in claim 22, the pack comprising the delivery system and a tray configured to releasably hold the pod of the catheter and the loading device in a cooperative juxta-position on the tray.

25. A catheter assembly as claimed in claim 15 wherein the deployer includes a guidewire.

26. A method for deploying a medical device at a desired location in a vasculature, the method comprising the steps of:
providing a medical catheter, the catheter comprising an elongate tubular portion having a proximal end and a distal end, the distal end of the tubular portion including a pod capable of receiving the medical device; and a deployer engageable with the medical device;
providing a loading device for collapsing the medical device from an expanded in-use position to a collapsed position for reception within the pod, the loading device having an inlet end and an outlet end;
engaging the outlet end of the loading device within the pod;
engaging the medical device with the deployer;
retracting the deployer proximally through the tubular portion, to draw the medical device through the loading device into the pod, thereby collapsing the medical device;
disengaging the loading device from the pod;
inserting the catheter into the vasculature and advancing the catheter through the vasculature until the pod is at the desired location;
deploying the medical device at the desired location.

27. A method as claimed in claim 26 wherein the medical device is deployed by moving the tubular portion proximally relative to the deployer.

28. A method as claimed in claim 26 including the step of withdrawing the tubular portion from the vasculature after deployment of the medical device.

29. A method as claimed in claim 26 wherein the deployer includes a guidewire.

30. A delivery system for transvascular deployment of a medical device comprising:
a catheter assembly comprising:
a catheter including a first portion and a second portion, the first portion including an elongate tubular body having a proximal end portion and a distal end portion, the second portion extending from the distal end portion of the first portion and forming a tubular pod capable of receiving a medical device; and
a deployer movable through the pod and coupled to the medical device to assist in moving the medical device between a stored position within the pod and an in-use position external of the pod,
the pod having a maximum wall thickness that is less than a minimum wall thickness of the distal end portion of the tubular body; and
a separate loading device which is operable to collapse the medical device from an expanded in-use Position to a collapsed position for reception within a pod, the loading device comprising a funnel having an enlarged inlet end and a narrowed outlet end, the outlet end being engageable with the pod.

31. A catheter assembly as claimed in claim 30 wherein the tubular body has an inner tubular core encased within a concentric tubular outer sheath which is fixed to the core, the sheath extending from a distal end of the core to form the pod.

32. A catheter assembly as claimed in claim 31 in which the tubular outer sheath is manufactured from a relatively low friction material.

33. A catheter assembly as claimed in claim 30 wherein the pod is integrally formed with the tubular body.

34. A catheter assembly as claimed in claim 30 wherein the wall thickness of the pod is less than or equal to 0.004 inches (0.1 mm).

35. A medical catheter pack for a delivery system of the type claimed in claim 30, the pack comprising the delivery system and a tray configured to releasably hold the pod of the catheter and the loading device in a cooperative juxta-position on the tray.

36. A catheter assembly as claimed in claim 30 wherein the deployer includes a guidewire.

37. A delivery system for transvascular deployment of a medical device comprising:

a catheter assembly comprising:

a catheter including a first portion and a second portion, the first portion including an elongate tubular body having a proximal end portion and a distal end portion, the second portion extending from the distal end portion of the first portion and forming a tubular pod capable of receiving a medical device; and a deployer movable through the pod and coupled to the medical device to assist in moving the medical device between a stored position within the pod and an in-use position external of the pod, the pod having a greater flexibility than the distal end portion of the tubular body; and a separate loading device which is operable to collapse the medical device from an expanded in-use position to a collapsed position for reception within a pod, the loading device comprising a funnel having an enlarged inlet end and a narrowed outlet end, the outlet end being engageable with the pod.

38. A catheter assembly as claimed in claim 37 wherein the tubular body has an inner tubular core encased within a concentric tubular outer sheath which is fixed to the core, the sheath extending from a distal end of the core to form the pod.

39. A catheter assembly as claimed in claim 38 in which the tubular outer sheath is manufactured from a relatively low friction material.

40. A catheter assembly as claimed in claim 37 wherein the pod is integrally formed with the tubular body.

41. A catheter assembly as claimed in claim 37 wherein the wall thickness of the pod is less than or equal to 0.004 inches (0.1 mm).

42. A medical catheter pack for a delivery system of the type claimed in claim 37, the pack comprising the delivery system and a tray configured to releasably hold the pod of the catheter and the loading device in a cooperative juxta-position on the tray.

43. A catheter assembly as claimed in claim 37 wherein the deployer includes a guidewire.

\* \* \* \* \*

UNITED STATES PATENT AND TRADEMARK OFFICE
CERTIFICATE OF CORRECTION

PATENT NO. : 6,752,819 B1
DATED : June 22, 2004
INVENTOR(S) : Eamon Brady et al.

It is certified that error appears in the above-identified patent and that said Letters Patent is hereby corrected as shown below:

Column 8,
Line 3, replace "nod," with -- pod, --; and

Column 10,
Line 50, replace "Position" with -- position --.

Signed and Sealed this

Twenty-eighth Day of September, 2004

JON W. DUDAS
*Director of the United States Patent and Trademark Office*